United States Patent
Dolgopyatov et al.

(10) Patent No.: US 9,778,182 B2
(45) Date of Patent: Oct. 3, 2017

(54) DEVICE AND METHOD FOR MONITORING FLUID IN SUBSEA EQUIPMENT

(71) Applicant: Siemens Aktiengesellschaft, Munich (DE)

(72) Inventors: Dmitry Dolgopyatov, Moscow (RU); Ivan Nikolin, Moscow (RU)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/889,585

(22) PCT Filed: May 7, 2013

(86) PCT No.: PCT/RU2013/000385
§ 371 (c)(1),
(2) Date: Nov. 6, 2015

(87) PCT Pub. No.: WO2014/182190
PCT Pub. Date: Nov. 13, 2014

(65) Prior Publication Data
US 2016/0077003 A1    Mar. 17, 2016

(51) Int. Cl.
G01N 21/00 (2006.01)
G01N 21/41 (2006.01)
G01J 3/28 (2006.01)
G01N 21/552 (2014.01)
G01N 21/85 (2006.01)

(52) U.S. Cl.
CPC .......... *G01N 21/552* (2013.01); *G01N 21/41* (2013.01); *G01N 21/8507* (2013.01)

(58) Field of Classification Search
CPC .. G01N 21/552; G01N 21/41; G01N 21/8507; G01N 21/431; G01N 21/53; G01N 21/474; G01N 2021/8528; E21B 47/00; E21B 47/123; G01V 3/30
USPC ......... 356/436, 128, 326, 73, 136, 442, 133; 250/339.11; 385/12, 13, 123, 48; 73/152.55
See application file for complete search history.

(56) References Cited

U.S. PATENT DOCUMENTS

| 4,887,879 A | 12/1989 | Prucnal et al. |
|---|---|---|
| 5,966,477 A | 10/1999 | Johnson |
| 6,118,520 A | 9/2000 | Harner |
| 2009/0034901 A1 | 2/2009 | Takabayashi et al. |
| 2010/0097682 A1* | 4/2010 | Angeley .......... A61F 9/00821 359/227 |
| 2010/0177310 A1 | 7/2010 | Difoggio |

(Continued)

FOREIGN PATENT DOCUMENTS

| CN | 201859115 U | 6/2011 |
|---|---|---|
| EP | 2 431 730 | 3/2012 |
| WO | WO 2010/100422 | 9/2010 |

*Primary Examiner* — Sunghee Y Gray
(74) *Attorney, Agent, or Firm* — Cozen O'Connor

(57) ABSTRACT

Monitoring device and method for monitoring a fluid in subsea equipment, wherein the monitoring device includes a sensing element in contact with the fluid, at least one detector and a waveguide, where the sensing element is configured to implement an evanescent field absorption technique, the at least one detector is configured to detect an attenuated optical signal fed into the waveguide by at least one radiation source, and where the attenuation is caused by evanescent field absorption due to the fluid.

13 Claims, 6 Drawing Sheets

(56) References Cited

U.S. PATENT DOCUMENTS

2011/0267603 A1 11/2011 Shaw
2012/0170023 A1* 7/2012 Szobota ............... G01N 21/552
356/51

* cited by examiner

DEVICE AND METHOD FOR MONITORING FLUID IN SUBSEA EQUIPMENT

CROSS-REFERENCE TO RELATED APPLICATIONS

This is a U.S. national stage of application No. PCT/RU2013/000385 filed 7 May 2013.

BACKGROUND OF THE INVENTION

1. Field of the Invention

The invention relates to a method and monitoring device for monitoring fluid in subsea equipment, where the monitoring device comprises a sensing element which is in contact with the fluid.

2. Description of the Related Art

Quality monitoring of liquids in remote apparatus and constructions, in particular in subsea equipment, is a challenging task. Such equipment can comprise transformers, power grids, switchgears and the like. By monitoring the properties of such liquids, for example their acidity, or water content a forecast can be made on the aging process of the liquids and the entire apparatus or construction.

It may, for example, be desirable to monitor the quality of a dielectric, i.e., electrically insulating, fluid in subsea equipment that contains electrical elements. Such a dielectric fluid can in particular be a transformer oil that is usually a highly refined mineral oil or a synthetic ester that is stable at high temperatures and has excellent electrical insulating properties. Such dielectric fluids are, for example, used in oil-filled transformers, high voltage capacitors, fluorescent lamp ballasts, high voltage switches and circuit breakers. The functions of the dielectric fluid comprise electrical insulation, suppression of corona and arcing, cooling and for several use cases such as subsea applications to provide pressure compensation.

Since the 1990s, on-line monitoring of dielectric fluids in transformers has become increasingly popular to reduce the number of time-consuming diagnostic operations. There are many techniques that have been developed and implemented to meet the demands of operating companies regarding both monitoring and diagnostics methods. The most common methods are presented in the following.

One known method is dissolved gas analysis (DGA). In dissolved gas analysis, the concentrations of $H_2$, $CH_4$, $C_2H_6$, $C_2H_4$, $C_2H_2$, $CO$ and $CO_2$ are measured to detect a degradation of the transformer fluid that might lead to a fault. Within the remote condition, monitoring DGA based systems implement either gas chromatography, for example, utilizing the SITRAM© gas chromatograph by Siemens, or photo-acoustic spectroscopy, for example, utilizing a Kelman monitoring device by General Electric. Both techniques require dissolved gases separation from the transformer oil. This is not feasible under high pressure.

Another method is partial discharge (PD) monitoring utilizing glass fiber rods, electrical methods, for example, utilizing RF coils or phase impulse current, or acoustic methods. Such PD activity monitoring is a convenient tool to detect the transformer fluid insulation degradation. Nevertheless, it does not provide any information on the composition of dielectric fluid contaminants. Also, PD monitoring is not utilized in a high pressure environment such as the subsea environment.

There are also methods for detecting the cellulose and oil moisture content, for example, via dielectric response analysis, capacitive probes, fiber optical methods and the Karl Fischer titration.

Other methods focus on the degree of polymerization (DP) by the utilization of paper samples and furanic compounds analysis. Also, there are acidity tests and dielectric strength tests. Karl Fischer titration, DP measurements with paper samples, acidity tests and dielectric strength tests are not feasible for in-situ implementation. Dielectric response analysis requires transformer shutdown. Further a capacitive sensor with the specification MMT162 for determining moisture in oil is available from Vaisala, with a metal version withstanding a pressure up to 200 bar. Even such a sensor is not sufficient for all subsea environments and furthermore it just allows for determination of moisture content.

There are also methods utilizing spectroscopy or transparency measurements in the ultraviolet-visible (UV VIS) or the near infrared (NIR) or the mid infrared spectral (MIR) spectral range.

For example, the MIR spectroscopy is a standardized technique for the inspection of insulating oil in the laboratory. However, this inspection is not intended for the determination of the various constituents of an oil (see ASTM D 2144). The technique is more developed for lubricants (see ASTM E 2412).

Further, document CN 201859115 describes optical absorption measurements utilizing a waveguide designed for multichannel fluid spectrum analyzation. However, this analyzer is not adapted for subsea applications.

Therefore, up-to-date commercially available hardware is not designed for monitoring a fluid, in particular a dielectric fluid, in subsea equipment, and therefore maintenance issues related to the condition of such a fluid remain unresolved.

SUMMARY OF THE INVENTION

It is therefore an object of the present invention to provide a monitoring device and a method of the initially mentioned type by which reliable monitoring in a harsh environment is feasible.

This and other objects and advantages are achieved in accordance with the invention by a method and monitoring device that includes at least one detector and a waveguide, where the sensing element forms a region of the waveguide, which is at least partially free of a cladding. The at least one detector is configured to detect an attenuated optical signal fed into the waveguide by at least one radiation source, where the attenuation is caused by evanescent field absorption due to the fluid. The evanescent field absorption (EFA) technique is based on the attenuated total reflectance effect. Evanescent waves emerge at a boundary between two media with different optical properties under total internal reflection conditions.

In the monitoring device with the sensing element being in contact with the fluid, the boundary between the two media is the boundary between the sensing element and the fluid, where the fluid has a lower refractivity than the sensing element and the angle of incidence of the optical signal is such that total reflectance occurs. The attenuation of the evanescent wave is a function of the refraction indices of the sensing element and the fluid, the geometry of the waveguide in the region of the sensing element and the absorption properties of the fluid at the locations where the evanescent waves emerge.

The configuration of the monitoring device is based on the finding that a change of the refraction index of a fluid due to the degradation of the fluid results in differences of the attenuation of the optical signal that is fed into the waveguide. Such a monitoring device in particular enables a condition or quality monitoring of a dielectric fluid under subsea conditions based on the measurement of the absorptive properties of the dielectric fluid via the EFA technique. Such a sensing technique for the monitoring of the aging of a fluid is reliable, and the sensing element is not sensitive to electromagnetic noise. Also, the sensing element is able to withstand the conditions of a harsh environment with high pressure, in particular a pressure of up to 300 bar, and elevated temperature conditions.

Furthermore, the monitoring device is cost effective and safe and therefore particularly useful for quality monitoring of an isolating fluid in remote equipment, in particular subsea equipment. As light absorption in the examined fluid is monitored, changes in fluid properties can be detected without an intervention into the work regime of the equipment containing the fluid. Also, the installation of an optical waveguide with the sensing element enables remote monitoring in a particularly easy way.

The aging of the equipment can be determined so that failures resulting in expensive repair or replacement of the entire equipment can be avoided. Also potential faults of the equipment can be detected at a very early stage, thus enabling a fast remedial response. As the sensor is resistant to electromagnetic noise, it is particularly suitable for fluids utilized in electrical equipment.

Additionally, the installation costs of the sensor are low, and the sensing element can easily be adapted to a variety of subsea apparatus and constructions. Moreover, the technology is well suited for high pressure conditions as they are present in subsea equipment.

In an advantageous embodiment, the monitoring device further comprises a plurality of radiation sources. Utilizing more than one radiation source enables multiple contaminants analysis and also the collection of baseline data, because the absorption and the scattering of the optical signal due to the intrinsic properties of the fluid can be determined.

The at least one radiation source can in particular be configured to feed the optical signal in the ultraviolet visible (UV-VIS) and/or the near infrared (NIR) and/or the mid infrared (MIR) spectral range. These spectral ranges have been proven to be particularly useful for detecting contaminants expected to be present in a fluid.

It has further proven to be advantageous, if each one of the plurality of radiation sources is configured to feed the optical signal into the waveguide over a range of wavelengths corresponding at least partially to wavelengths being to a larger extent attenuated by a specific contaminant in the fluid than by other contaminants. In other words, radiation sources fitting specific bandwidths of interest enable monitoring multiple contaminants. The monitoring on several wavelengths allows a particularly precise determination of a particular pollutant or contaminant by measuring the absorption near the absorption wavelengths of the contaminant. Determining a baseline or reference absorption improves the accuracy and excludes contributions from scattering and measuring equipment aging. Also the concentrations of a variety of different pollutants can be determined in real time by utilizing radiation sources that feed specific wavelengths into the waveguide.

Baseline data collection yields a higher accuracy of the measurement and provides for multiple component analysis.

The multiple component analysis provides for discrimination between different aging mechanisms. This allows to determine the degree and the scenario or reason of the degradation of the fluid's isolating properties. In such a way, the proper time for an intervention in order to change or repair the equipment can be readily predicted. Also the utilization of multiple radiation sources avoids an installation of a spectrometer.

It is further advantageous, if a coupling element is provided, which is configured to merge a plurality of transmission lines from the plurality of radiation sources into a part of the waveguide, which comprises the sensing element. Such an optical coupler renders the design of the monitoring device particularly simple, as the same sensing element can be utilized with the plurality of radiation sources.

In a further advantageous embodiment of the monitoring device, an optical splitter is provided, which is configured to distribute the attenuated optical signals of the plurality of radiation sources to a plurality of detectors. Additional detectors are implemented, if the spectral ranges of all the radiation sources are not covered with one detector or for redundancy reasons.

The radiation source and the detector can be operated under normal pressure, for example, if they are installed onshore or inside a subsea enclosure with atmospheric pressure or a pressure in between subsea pressure and atmospheric pressure. This allows the utilization of commercially available radiation sources and detectors without any modification.

On the other hand, a particularly reliable and robust monitoring device can be obtained, if at least one radiation source and the at least one detector are at least partially submerged in the fluid and designed to withstand a pressure existing in the fluid.

If the radiation sources and the detectors are configured to withstand a pressure of 300 bar, utilization of the monitoring device in a variety of subsea environments is feasible.

For the operation of the radiation sources and the detectors, a control unit may be provided. The control unit is preferably configured to shut down the at least one radiation source or to operate it in a standby mode when no monitoring of the fluid is desired. With the control unit, the at least one radiation source may thus be activated on demand, and the radiation sources do not need to be operated permanently. This reduces the energy requirement of the monitoring device and extends the lifetime of the monitoring device.

The control unit can also be configured to turn on each one of a plurality of radiation sources one after another, if the monitoring device comprises multiple radiation sources. Thus, the accurate detection of multiple contaminants in the fluid can be controlled by the control unit.

It is advantageous, if the control unit is at least partially submerged in the fluid and configured to withstand a pressure existing in the fluid, in particular a pressure of 300 bar. This allows for a very compact design of the monitoring device.

It is possible that some parts of the monitoring device may not be installed within the fluid due to space constraints or for other reasons. In such cases, an optical penetrator may be provided which enables passing the waveguide with the region serving as sensing element into the fluid to be monitored.

In a further embodiment, a planar waveguide with a plane surface being in contact with the fluid can also be utilized, and attenuated total reflectance (ATR) can be measured.

Alternatively, the sensing element can be provided by a region of the optical fiber with at least partially removed cladding around a core. Such a waveguide can particularly easily be brought into a desired geometry suitable for implementation of the evanescent field absorption technique.

If the waveguide is configured as the optical fiber, the monitoring device can comprise at least one mode scrambler which is configured to provide a plurality of bends in the optical fiber. Such a mode scrambler is useful for an optimization of light power distribution across the cross section of the fiber. This increases the signal-to-noise ratio. The reason for this increase is that the bends tend to couple out higher-order radiation modes, and thus the optical signal is distributed in a plurality of modes that will remain stable over long distances. Additionally or alternatively, other devices may be utilized to increase the signal-to-noise ratio.

In the method according to the invention, a fluid in subsea equipment is monitored. Therefore, a sensing element is brought into contact with the fluid. An optical signal is fed into a waveguide, and the sensing element is configured as a region of the waveguide, which is at least partially free of a cladding. An attenuation of the optical signal fed into the waveguide is detected by at least one detector, and the attenuation is caused by evanescent field absorption by the fluid. The evanescent field absorption technique utilized for monitoring the fluid in the subsea equipment enables remote observation of a degradation or deterioration of the fluid under subsea pressure conditions.

The preferred embodiments presented with respect to the monitoring device and the advantages thereof correspondingly apply to the method for monitoring the fluid and to the utilization of the monitoring device.

The features and feature combinations mentioned above in the description as well as the features and feature combinations mentioned below in the description of figures and/or shown in the figures alone are usable not only in the respectively specified combination, but also in other combinations or alone without departing from the scope of the invention.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

Further advantages, features and details of the invention are apparent from the claims, the following description of preferred embodiments as well as based on the drawings, in which identical or functionally identical elements are provided with identical reference characters, in which:

DETAILED DESCRIPTION OF THE EXEMPLARY EMBODIMENTS

Figure 1:
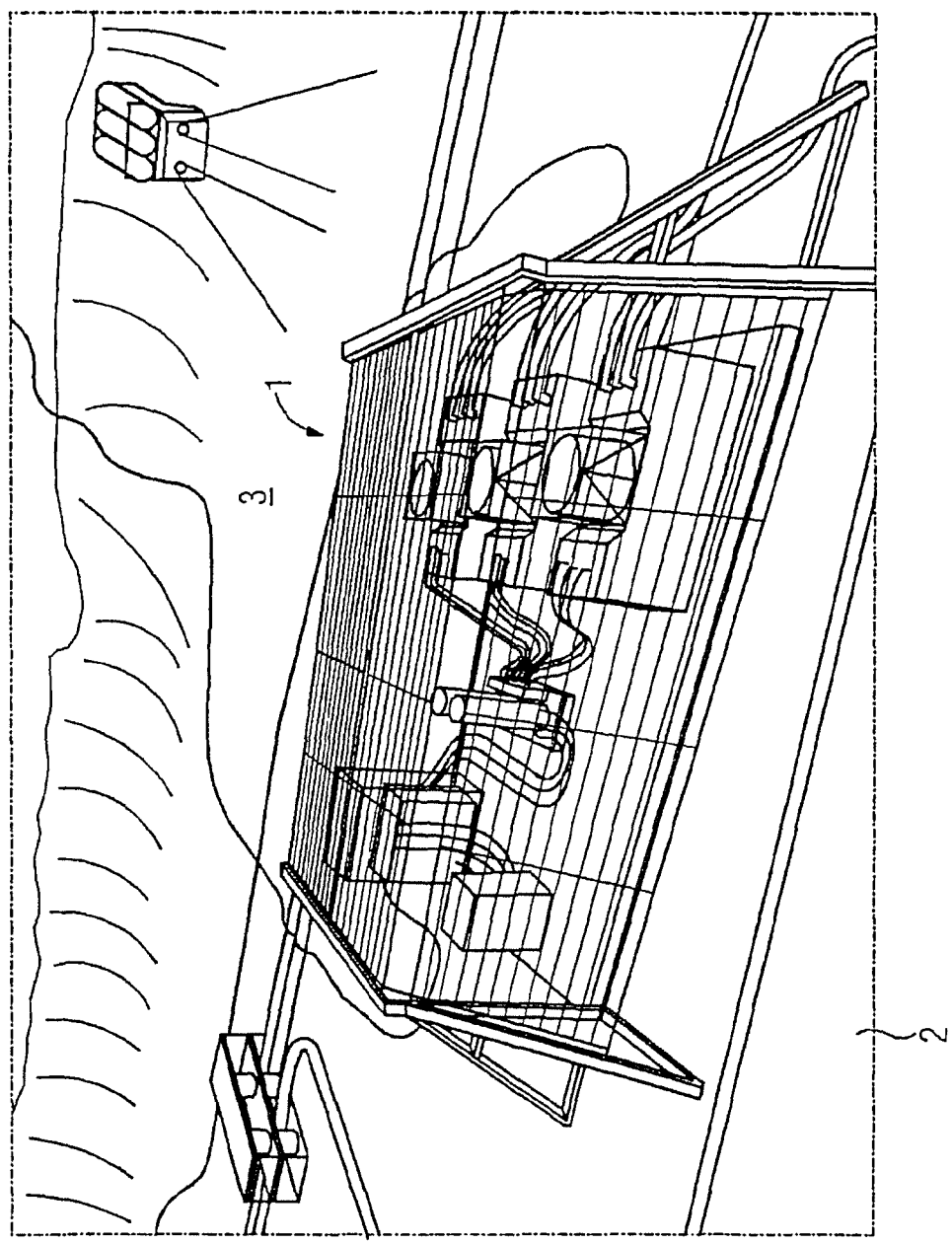
FIG. 1 shows a subsea power grid construction as an example of subsea equipment containing a dielectric fluid to be monitored.

FIG. 1 shows an example of subsea equipment 1, i.e. equipment located on the seafloor 2. Consequently, the power grid 1 is surrounded by water 3. The subsea equipment 1 comprises electrical elements containing a dielectric fluid 4 (see FIG. 2) such as a transformer oil.

Figure 2:
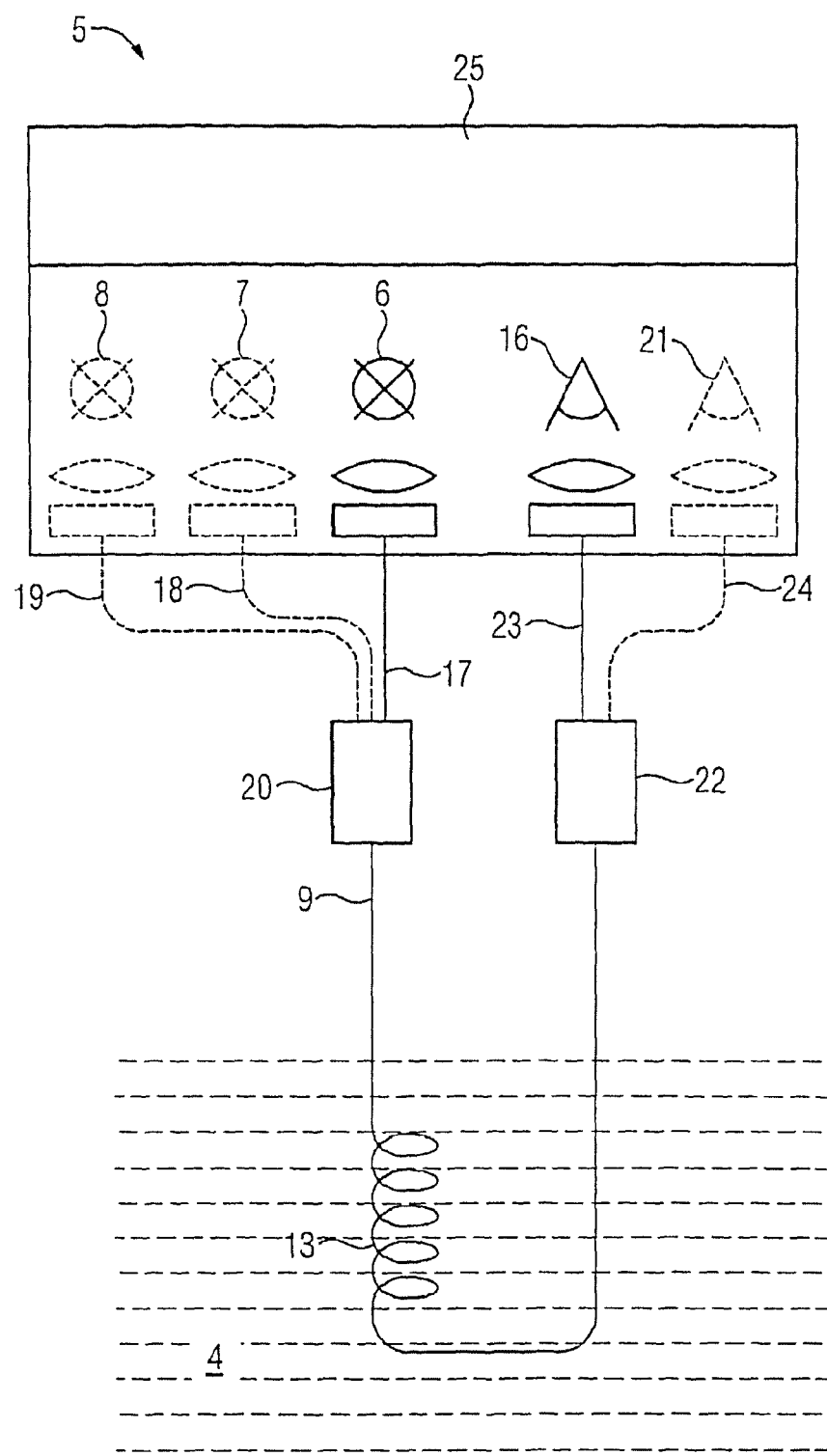
FIG. 2 schematically shows a monitoring device comprising a waveguide with a sensing element which is in contact with the fluid in accordance with the invention.

This fluid 4 is schematically represented in FIG. 2. As the degradation of the fluid 4 can influence the performance and functionality of the subsea equipment containing the fluid 4, the quality of this fluid 4 is monitored.

To achieve this, a monitoring device 5 is utilized, which is also schematically represented in FIG. 2. The monitoring device 5 preferably comprises several radiation sources 6, 7, 8. These radiation sources 6, 7, 8, feed optical signals into a waveguide 9. The waveguide 9 is, for example, an optical fiber comprising a core 10 and a cladding 11 with slightly lower refractive index (see FIG. 3).

In a region 12 of the waveguide 9 serving as a sensing element 13 (see FIG. 2) the optical fiber is bare of the cladding 11 and is therefore in contact with the fluid 4. In other words, the cladding 11 is removed from the waveguide 9 in the region 12 that serves as the sensing element 13.

Figure 3:
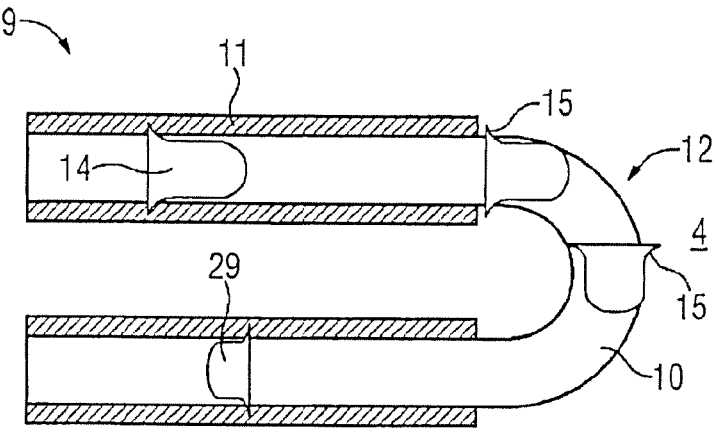
FIG. 3 schematically shows a part of the waveguide comprising the sensing element, where a core of an optical fiber that serves as the waveguide is bare of a cladding in accordance with the invention.

Optical signals 14 provided by one of the radiation sources 6, 7, 8 traveling through the optical fiber 10 are schematically shown in FIG. 3. In the region 12, where the optical fiber is uncladded, total reflection of the optical signal 14 occurs at the boundary between the core 10 and the fluid 4. This is due to the different refraction indices of the core 10 of the optical fiber and the fluid 4 as well as the angle of incidence of the optical signal 14. Under the conditions of total reflection, evanescent waves 15 emerge at the boundary between the bent optical fiber 14 and the fluid 4.

Due to this absorption of a part of the optical signal 14 by the fluid 4, a detector 16 of the monitoring device 5 detects an attenuated optical signal 29. As the absorption properties of the fluid 4 vary in function of the presence of contaminants and the aging of the fluid 4, by utilizing the evanescent field absorption technique the quality of the fluid 4 can be monitored with the monitoring device 5.

The features of the sensing element 13, for example, its geometry, are optimized for the specific operating conditions with respect to the monitored fluid 4, the type of waveguide 9 and the bandwidth of the optical signals 14. Providing a plurality of radiation sources 6, 7, 8 allows the collection of baseline data and therefore allows the intrinsic absorption or scattering properties of the fluid 4 to be taken into account. From the different radiation sources 6, 7, 8, respective transmission lines 17, 18, 19 lead to a coupling element in form of an optical coupler 20. The waveguide 9 is connected to this optical coupler 20 and thus receives the particular optical signals 14 or optical waves provided by each one of the radiation sources 6, 7, 8.

Especially if a plurality of radiation sources 6, 7, 8 is utilized, it is also possible to use a plurality of detectors 16, 21 as shown in FIG. 2. In this way, the specific detector 16, 21 can be configured to detect the optical signals 14 of a predetermined number of wavelengths or bandwidths.

If a plurality of detectors 16, 21 is utilized, an optical splitter 22 can be connected to the waveguide 9 downstream of the sensing element 13. This optical splitter 22 distributes the attenuated optical signals 14 to the appropriate detector 16, 21 via transmission lines 23, 24 coupled to the optical splitter 22.

As shown in FIG. 2 parts of the monitoring device 5 can be situated outside a compartment of a transformer or such a component of the power grid 1, which contains the fluid 4. In such a case, optical penetrators can be utilized in order to introduce the waveguide 9 into the fluid 4 while other parts of the monitoring device 5 are not submerged in the fluid 4.

The monitoring device 5 also comprises a control unit 25 which operates the radiation sources 6, 7, 8 and the detectors 16, 21. The control unit 25 can, for example, put the radiation sources 6, 7, 8 on standby or turn the radiation sources 6, 7, 8 off for prolonged periods of time and activate the radiation sources 6, 7, 8 just when monitoring of the fluid 4 is required. Also the control unit can turn on the radiation sources 6, 7, 8 subsequently.

In an advantageous embodiment of the monitoring device 5, the radiation sources 6, 7, 8, the detectors 16, 21 and the control unit 25 are submerged into the fluid 4 and configured to withstand high pressure, i.e., a pressure of up to 300 bar. Thus, a very robust monitoring device 5 is provided.

It is also possible to utilize several monitoring devices 5 with respective sensing elements 13 or to utilize a monitoring device 5 with several sensing elements 13. This enhances reliability and accuracy and avoids false signals.

As shown in FIG. 3, in the section or region 12 of the waveguide 9, where the cladding 11 of the optical fiber 10 is removed, the evanescent waves 15 propagate in the fluid 4 to be examined. The parts of the optical signals 14 situated in the fluid 4 in FIG. 3 schematically illustrate the optical power distribution and thus the evanescent field absorption.

The resulting signal attenuation will be a function of the properties of this fluid 4 and the design of the sensing element 13. The geometry of the sensing element 13 is optimized for the particular application. However, it is desirable to assure that the optical signals 14 travel in an undisturbed manner to the region 12 and from the region 12 to the detectors 16, 21.

Figure 4:
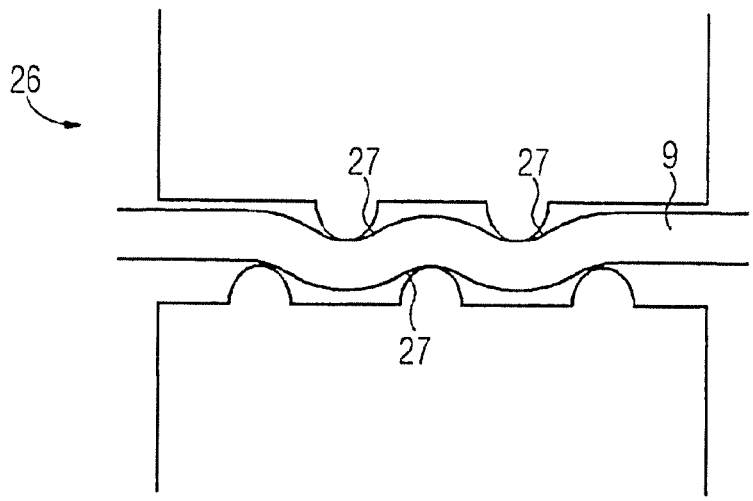
FIG. 4 shows a mode scrambler that may be utilized for the waveguide of FIG. 3.

Accordingly FIG. 4 shows a mode scrambler 26, which can be utilized to form bends 27 in the optical fiber utilized as the waveguide 9. This results in an optimized light power distribution over the cross section of the optical fiber, where the distribution of modes will remain stable over long distances.

Figure 5:
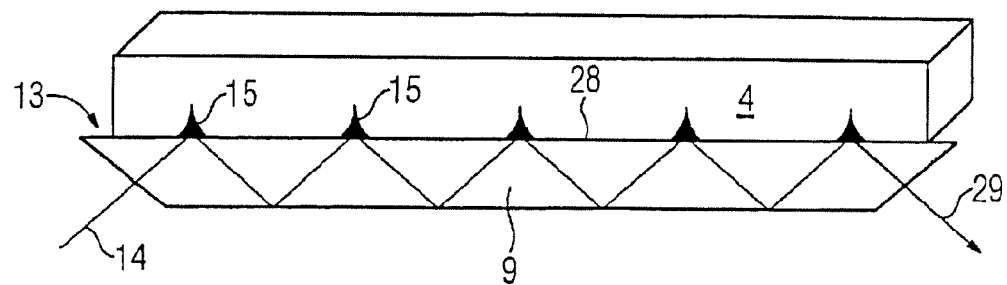
FIG. 5 schematically shows an alternative configuration of a waveguide to be utilized with the monitoring device of FIG. 2.

FIG. 5 shows an alternative sensing element 13 design where it is configured as a planar waveguide 9 having a planar surface 28 being in contact with the fluid 4. Utilizing such a planar waveguide 9, instead of the optical fiber with removed cladding 11, also allows the detection of attenuated optical signals with the detectors 16, 21. The optical signal 14 coming from one of the radiation sources 6, 7, 8 is shown to produce evanescent waves 15 at the boundary between the planar surface 28 of the waveguide 9 and the fluid 4. The attenuated signal 29 is then conveyed to one of the detectors 16, 21.

The sensing element 13 schematically shown in FIG. 5 is also configured to implement the evanescent field assorption (EFA) technique as the attenuation of the optical signal is based on the attenuated total reflectance (ATR).

In particular bandwidths or wavelengths in the UV-VIS, NIR or MIR spectral ranges may be utilized to detect impurities in the dielectric fluid 4.

As an example, a dielectric fluid 4 has been investigated using optical absorption spectroscopy. This dielectric fluid 4 is a synthetic pentaerythritol ester that is utilized as the transformer dielectric fluid. The reference oil or fluid 4 is considered clear.

There are several contaminants that may be present in this fluid 4. These include but are not limited to the following: water, ester base-stock breakdown products such as carboxylic acid and pentaerythritol. Also, dissolved carbon dioxide can be present as a contaminant in the fluid 4 and detected with the monitoring device 5.

Accordingly, there are several bandwidths or wavelengths at which these contaminants show an attenuation of the optical signal 14 to a larger extent than at other wavelengths. Instead of the wavelengths, the wave number in $cm^{-1}$ can also be utilized to express the bandwidth of the optical signals 14 provided by the sources 6, 7, 8.

For example, well recognizable absorption bands for water are approximately between 5300 to 5220 $cm^{-1}$, 3700 to 3600 $cm^{-1}$, and 1640 to 1605 $cm^{-1}$. Wave numbers that are particularly appropriate to detect the absorption of light energy via evanescent waves caused by carboxylic acids are approximately between 3560 and 3460 $cm^{-1}$, whereas the bandwidth to detect pentaerythritol is between 3400 and 3200 $cm^{-1}$. The bandwidth for dissolved carbon dioxide is approximately between 2345 and 2330 $cm^{-1}$.

Figure 6:
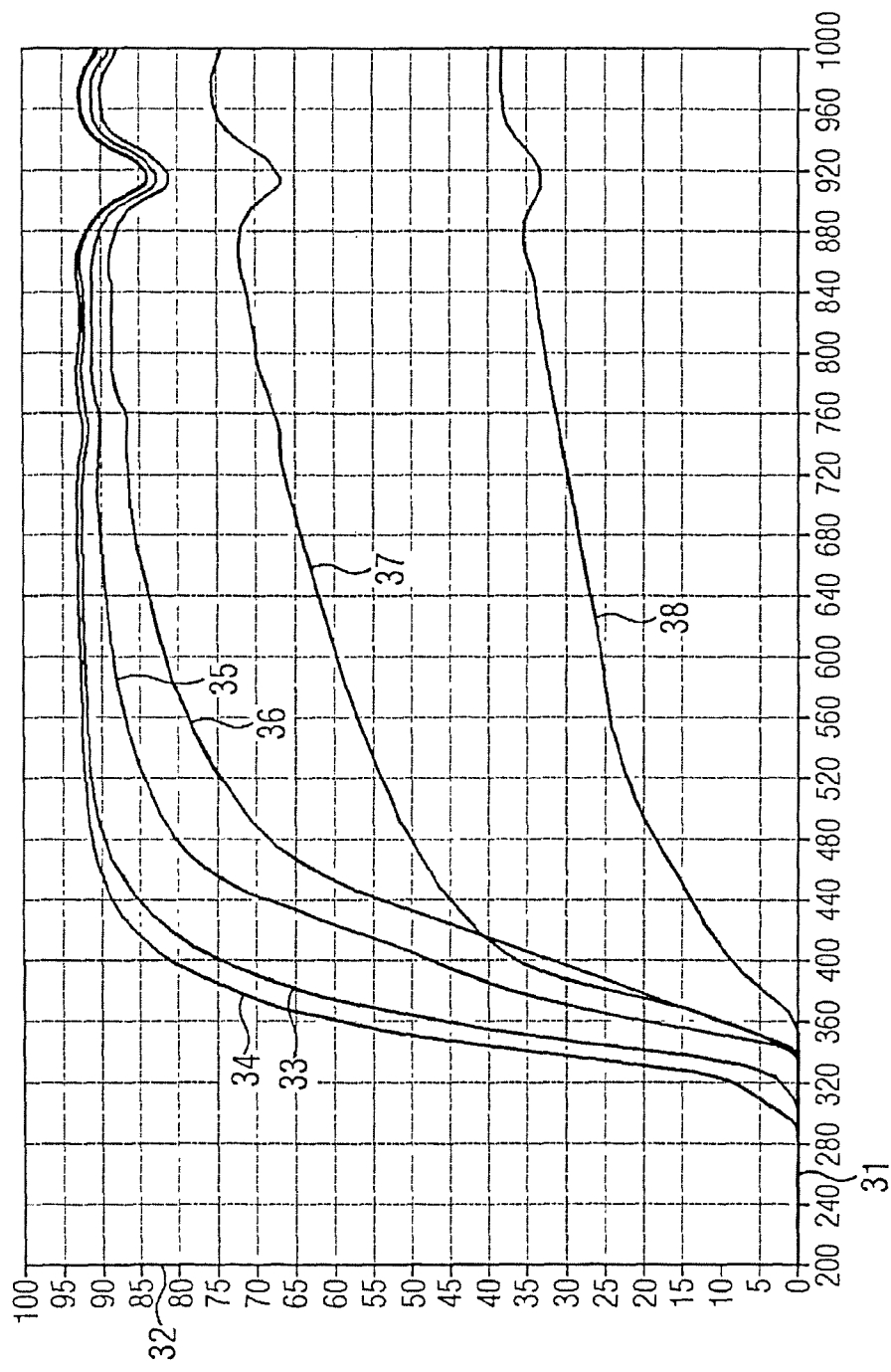
FIG. 6 is a graphical plot of the UV-VIS transmission spectra of samples of a dielectric fluid in different conditions and aging times.

FIG. 6 shows a graph 30 representing UV-VIS transmission spectra of samples of the investigated fluid 4, which are degraded in different conditions. On an abscissa 31 the wavelength in nm is indicated and on an ordinate 32 the transmission in percent. A curves 33, 34 represents the uncontaminated sample. Further curves 35, 36, 37, 38 represent the samples of different conditions or different aging times. As can be seen, for example, from the curve 38 the corresponding sample shows a much lower transmission over the entire range of wavelengths than the sample represented by the curve 33. This is due to the presence of contaminants and the aging of the fluid 4 in the corresponding sample.

Figure 7:
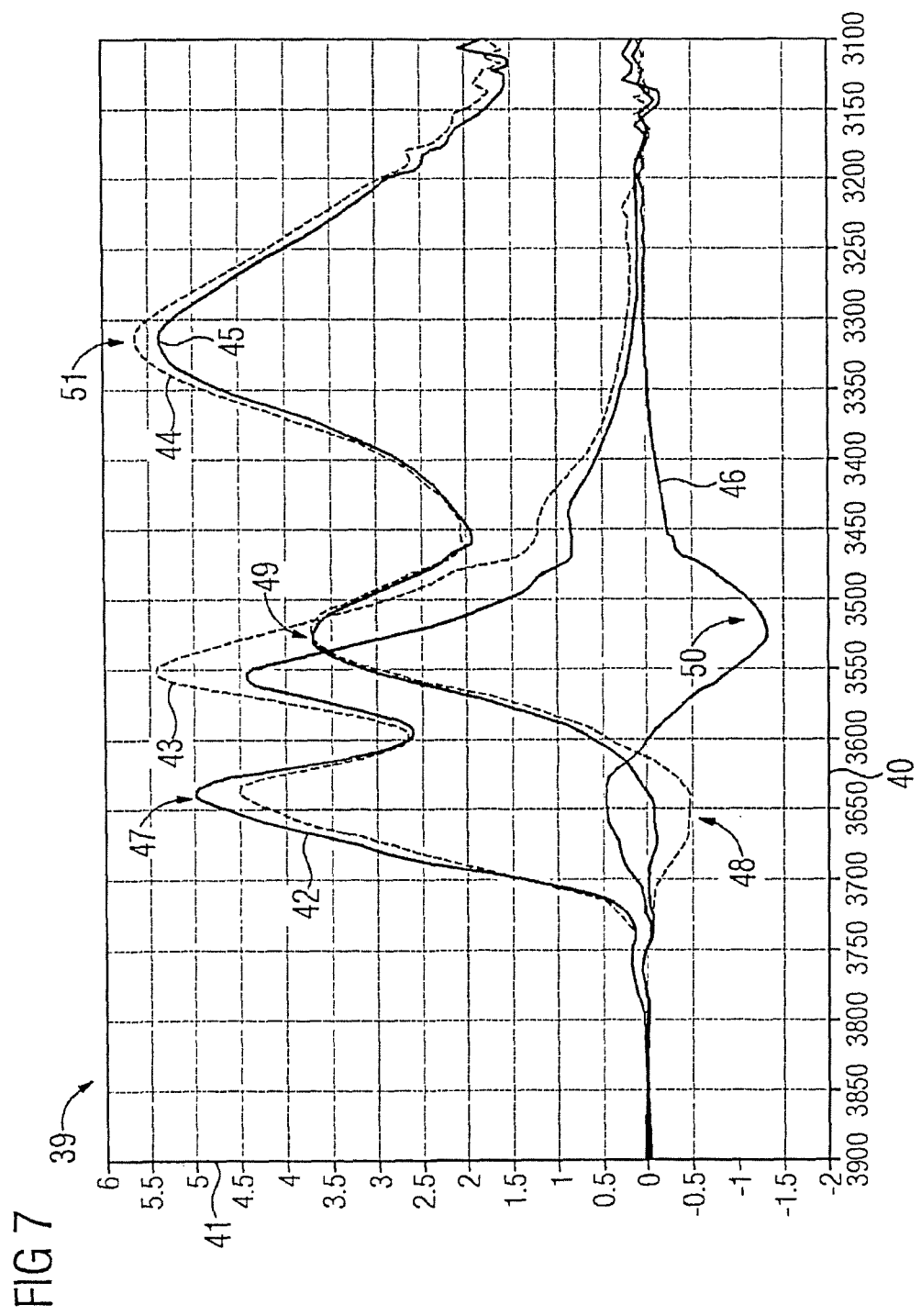
FIG. 7 is a graphical plot of the MIR differential absorption spectra of the samples according to FIG. 6.

FIG. 7 shows another graph 39 with MIR differential absorption spectra of the samples, where on an abscissa the wave number in $cm^{-1}$ is indicated and on an ordinate the absorption coefficient in $cm^{-1}$. In the graph 39 in FIG. 7, an uncontaminated sample is used as a reference and curves 42, 43, 44, 45, 46 represent a ratio between corresponding samples and the reference sample.

This differential absorption evaluation illustrates particularly well how the contaminants expected to be present in the samples can be determined. For example, deviations in the forms of peaks 47 or a minimum 48 in the curves 42, 43 and 44 respectively indicate the presence of water.

Other peaks 49 and a minimum 50 in curves 44, 45, 46 respectively indicate the presence of carboxylic acids in the samples. Finally, peaks 51 in the curves 44, 45 indicate the presence of pentaerythritol in two of the samples.

As can be seen from this evaluation of the differential absorption spectra, utilizing the multiple radiation sources 6, 7, 8 that fit the specific bandwidths of interest for the expected contaminants allows a multi component analysis of the samples and the discrimination between different aging mechanisms. For example, curve 44 and curve 45 in FIG. 7 correspond to samples having the same conditions, but different aging times. Thus, the degree of degradation as a function of the aging time can be readily determined with the evanescent field absorption technique.

The monitoring device 5 shown in FIG. 2 thus provides a cost effective, safe and reliable tool for quality monitoring of an isolating fluid 4 in a remote, and in particular subsea equipment. The monitoring device 5 utilizes the evanescent field absorption technique, in particular by implementing the optical fiber (see FIG. 3) or another waveguide 9 (see FIG. 5) to monitor light absorption in the examined fluid 4 at specific bandwidths under subsea conditions. The bandwidths comprise in particular wavelengths in the NIR, MIR or UV-VIS spectral range.

Figure 8:
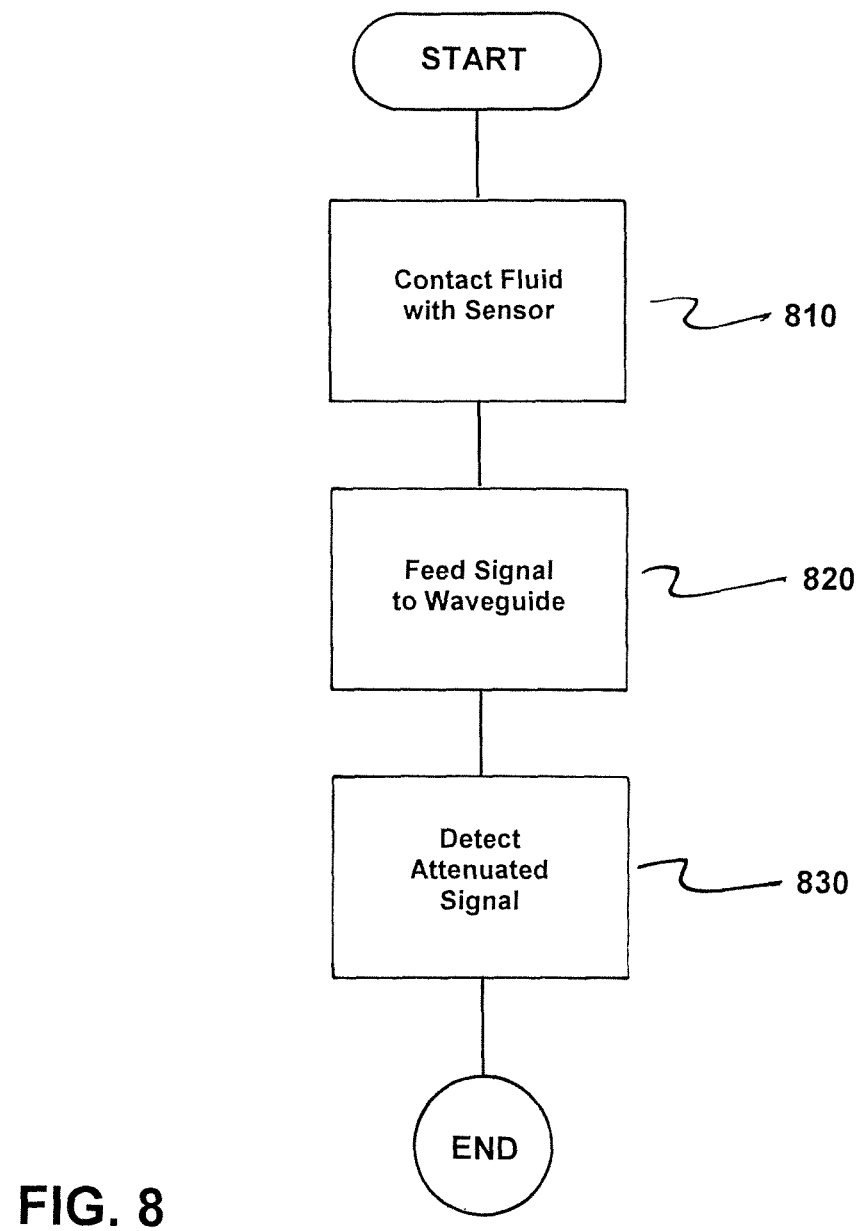
FIG. 8 is a flowchart of the method in accordance with the invention.

FIG. 8 is a flowchart of a method for monitoring a fluid (4) in subsea equipment (1) in accordance with the invention. The method comprises bringing a sensing element (13) into contact with the fluid (4), as indicated in step 810. Here, the sensing element (13) being configured to implement an evanescent field absorption technique. Next, an optical signal (14) is fed into a waveguide (9), as indicated in step 820. An attenuated optical signal (29) fed into the waveguide (9) is now detected by at least one detector (16, 21), as indicated in step 830. Here, the attenuation being caused by evanescent field absorption by the fluid (4).

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A monitoring device for monitoring a fluid in subsea equipment, comprising:
   a plurality of radiation sources;
   a control unit configured to one of (i) shut down at least one radiation source of the plurality of radiation sources when no monitoring of fluid to detect evanescent field effects is desired and (ii) operate the at least one radiation source in a standby mode when monitoring of fluid to detect evanescent field effects is undesired, and configured to turn on each of the plurality of radiation sources one after another;
   a sensing element in contact with the fluid and communicating with the radiation source via at least one first transmission line;
   a plurality of detectors communicating with the sensing element via an optical splitter and a plurality of second transmission lines; and
   a waveguide operatively coupled to the at least one first transmission line and the at least one second transmission line;
   wherein the sensing element forms a region of the waveguide, which is at least partially free of a cladding;
   wherein the plurality of detectors are configured to detect at least one attenuated optical signal fed into the waveguide by at least one radiation source of the plurality of radiation sources, the attenuation being caused by evanescent field absorption by the fluid.

2. The monitoring device according to claim 1, wherein each of the plurality of radiation sources is configured to feed the optical signal in at least one of (i) the ultraviolet-visible, (ii) the near infrared and (iii) the mid infrared spectral range.

3. The monitoring device according to claim 2, wherein each of the plurality of radiation sources is further configured to feed the optical signal into the waveguide over a range of wavelengths corresponding at least partially to wavelengths being to a larger extent attenuated by a specific contaminant in the fluid than by other contaminants.

4. The monitoring device according to claim 3, further comprising:
   a coupling element configured to merge a plurality of transmission lines from the plurality of radiation sources into a part of the waveguide which comprises the sensing element.

5. The monitoring device according to claim 2, further comprising:
   a coupling element configured to merge a plurality of transmission lines from the plurality of radiation sources into a part of the waveguide which comprises the sensing element.

6. The monitoring device according to claim 2, wherein the optical splitter is configured to distribute the attenuated optical signals of the plurality of radiation sources to the plurality of detectors.

7. The monitoring device according to claim 1, wherein the at least one radiation source and the plurality of detectors are at least partially submerged in the fluid and are configured to withstand a pressure existing in the fluid.

8. The monitoring device according to claim 7, wherein the pressure is 300 bar.

9. The monitoring device according to claim 1, wherein the control unit is at least partially submerged in the fluid and configured to withstand a pressure existing in the fluid.

10. The monitoring device according to claim 9, wherein the pressure is 300 bar.

11. The monitoring device according to claim 1, wherein the sensing element is provided by a region of an optical fiber with at least partially removed cladding around a core.

12. The monitoring device according to claim 11, wherein the monitoring device comprises at least one mode scrambler which is configured to provide a plurality of bends in the optical fiber.

13. A method for monitoring a fluid in subsea equipment, comprising:
   bringing a sensing element into contact with the fluid, the sensing element being configured to implement an evanescent field absorption technique;
   feeding an optical signal into a waveguide; and
   detecting, by at least one detector of a plurality of detectors, an attenuated optical signal fed into the waveguide, the attenuation being caused by evanescent field absorption by the fluid;
   wherein the sensing element communicates with a plurality of radiation sources via at least one first transmission line;

wherein the plurality of detectors communicate with the sensing element via an optical element and a plurality of second transmission lines; and wherein the waveguide is operatively coupled to the at least one first transmission line and the plurality of second transmission lines; and wherein a control unit one of (i) shuts down at least one radiation source of the plurality of radiation sources when no monitoring of fluid is desired to detect evanescent field effects and (ii) operates the at least one radiation source in a standby mode when monitoring of fluid to detect evanescent field effects is undesired, and turns on each of the plurality of radiation sources one after another.

\* \* \* \* \*